United States Patent [19]

Nemeth et al.

[11] Patent Number: 5,744,619

[45] Date of Patent: Apr. 28, 1998

[54] TITANOVANADOSILICALITES AS EPOXIDATION CATALYSTS FOR OLEFINS

[75] Inventors: Laszlo T. Nemeth, Palatine; Gregory J. Lewis, Mount Prospect; Richard R. Rosin, Arlington Heights, all of Ill.

[73] Assignee: UOP LLC, Des Plaines, Ill.

[21] Appl. No.: 818,265

[22] Filed: Mar. 17, 1997

[51] Int. Cl.⁶ ................................................. C07D 301/03
[52] U.S. Cl. .................................................. 549/523
[58] Field of Search ...................................... 549/523

[56] References Cited

U.S. PATENT DOCUMENTS

| | | | |
|---|---|---|---|
| 4,410,501 | 10/1983 | Taramasso et al. | 423/326 |
| 4,833,260 | 5/1989 | Neri et al. | 549/531 |
| 5,354,875 | 10/1994 | Nemeth et al. | 549/531 |
| 5,434,118 | 7/1995 | Caratari et al. | 502/242 |
| 5,466,835 | 11/1995 | Nemeth et al. | 549/531 |
| 5,591,875 | 1/1997 | Chang et al. | 549/531 |

FOREIGN PATENT DOCUMENTS

| | | | |
|---|---|---|---|
| 526945 | 7/1992 | European Pat. Off. | C07D 301/06 |

OTHER PUBLICATIONS

Notari, B., *Innovation in Zeolite Materials Science;* Grobet, P. J. et al., Ed.,; Elsevier: Amsterdam, pp. 422–424, 1980.

A.J.H.P. van der Pol et al., *Appl. Catal.*, A92 (1992), 113–130.

J. Kornatowski et al., *J. Chem. Soc. Faraday Trans.*, 91, 2217 (1995).

T–H. Chang et al., *Zeolites*, 15, 496 (1995).

*Primary Examiner*—C. Warren Ivy
*Assistant Examiner*—Garth M. Dahlen
*Attorney, Agent, or Firm*—Thomas K. McBride; Eugene I. Snyder

[57] ABSTRACT

Titanovanadosilicalites have been found to be very selective, active catalysts in the epoxidation of olefins by peroxides. Dilute hydrogen peroxide suffices to afford high yields of the epoxide. Vanadium incorporation at levels of Si:V in the range 100–2500 effectively changes the characteristics of the titanosilicalite into which it is incorporated to give near quantitative conversion of propylene at selectivities greater than 90%.

17 Claims, No Drawings

TITANOVANADOSILICALITES AS EPOXIDATION CATALYSTS FOR OLEFINS

BACKGROUND OF THE INVENTION

One of the most challenging and formidable tasks in preparative organic chemistry is the selective functionalization of hydrocarbons. Once a functional group has been introduced, the chemist has a rich selection of tools to achieve further transformations and transpositions, but the initial barrier of introducing a functional group is determinative of further chemistry. Not only is it necessary that a given functionalization reaction proceeds in good yield, but it is necessary also that it proceeds with specificity. One of the most chemically attractive entry points to functionalization of hydrocarbons is the carbon-carbon double bond in alkanes and substituted alkenes, for the carbon-carbon double bond undergoes many reactions which introduce functional groups onto one or both of the carbons, and the double bond also activates an adjacent C—H bond (i.e., allylic hydrogen) to still other reactions. Among the chemical reactions of the carbon-carbon double bond that of epoxidation occupies a special niche, because epoxidation is virtually unique to the C=C linkage, because epoxidation proceeds with great specificity, and because the resulting epoxide is a controllably reactive functional group which reacts with a wide range of reagents, schematically represented here as H—Y, to afford an equally wide range of difunctional materials according to the reaction,

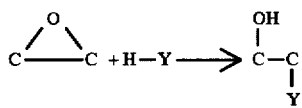

Although epoxidation may be performed with several different oxidizing agents, that variation of greatest interest here is one where the agent is a hydroperoxide. A commercial process uses tertiary butyl or ethylbenzene hydroperoxide in combination with 2% titania supported on silica to epoxidize propylene to propylene oxide with greater than 97% conversion of, for example, ethylbenzene hydroperoxide and selectivities to propylene oxide formation approaching 90%. See U.S. Pat. Nos. 3,642,833, 3,923,843, 4,021,454 and 4,367,342, all assigned to Shell Oil Company. More recently an Italian group has developed catalysts, referred to as titanium silicalites, where small amounts of framework silicon in silicalite are said to be replaced by titanium [Taramasso et al., U.S. Pat. No. 4,410,501] and has found such materials, conveniently designated as TS-1, to be effective in catalyzing the epoxidation of olefinic compounds by hydrogen peroxide in either the presence or absence of a solvent; U.S. Pat. No. 4,833,260. Subsequently this has been extended to the epoxidation of olefins with oxygen in air in the presence of a redox system of alkyl anthrahydroquinone and alkyl anthraquinone; EP 526,945.

Notari, B., Innovation in Zeolite Materials Science; Grobet, P. J. et al., Ed.,; Elsevier: Amsterdam, pp. 422–424 has speculated that the observed catalytic activity both of titania supported on silica and TS-1 arises from the high dispersion of titanium atoms in a silica lattice, that is, active materials are characterized by TI(IV) isolated by a long sequence of —O—Si—O—Si—. This conclusion was supported somewhat by the observation that when titania is supported on alumina, magnesia, or zirconia the resulting composite is inactive in epoxidation, and also is supported by the observation that catalyst activity increases as manifested by an increase in epoxide selectivity as the concentration of titania on silica decreases. Catalytic activity of TS-1 in the hydroxylation of phenol with $H_2O_2$ also has been shown to be dependent on particle size [A. J. H. P. van der Pol et al., Appl. Catal., A92 (1992), 113–130] with particles in the 0.2–0.3 micron range being 10 times more active than those in the 5 micron range.

More recently Nemeth et al. have shown that particular mixtures of a titanosilicate and titania are demonstrably more active and more selective as a catalyst in the epoxidation of olefinic compounds than are prior art titanium-based catalysts which have been used in epoxidation and have linked the improved catalytic qualities to the particle size of both the titanosilicate and titania; U.S. Pat. No. 5,466,835.

In the quest further improved oxidation catalyst, we have recently investigated titanosilicalite analogs which incorporate third metals into the molecular sieve structure and have found that vanadium incorporation at extremely low levels is quite effective in modifying catalyst properties. This is particularly surprising since vanadium incorporation into, e.g., silicalite affords material with little or no catalyst activity in oxidation whereas similar incorporation into, e.g., a titanosilicalite affords a substantial boost in activity. Additionally, we have determined that activity of titanovanadosilicalites is quite dependent on particle size, as is the case for the titanosilicates alone.

Although titanovanadosilicates have been reported [J. Kornatowski et al., J. Chem Soc. Farady Trans., 91, 2217 (1995); T-H. Chang et al., Zeolites, 15, 496 (1995)] these appear to have the MEL structure rather than the MFI structure of, e.g., a titanosilicate as TS-1. Furthermore, since vanadium (V) is known to be a potent oxidizing agent, it is important to extract all extraneous and weakly bound oxo-vanadium species prior to measuring its catalytic properties. This has not always been clear in the prior art; consequently the catalytic properties of, e.g., a titanovanadosilicate with MEL structure may not be inherent but rather the manifestation of extraneous oxo-vanadium species.

SUMMARY OF THE INVENTION

One purpose of this invention is to devise a facile, efficient process for the conversion of olefins generally to their epoxides in high yield and with great selectivity. One embodiment is the epoxidation of an olefinic compound by hydrogen peroxide using as a catalyst a titanovanadosilicalite, especially where the average particle size is no greater than about 0.5 microns. In a more specific embodiment the epoxidation is conducted using hydrogen peroxide at a concentration no more than about 30 weight percent. In a more specific embodiment the epoxidation is effected with hydrogen peroxide at a concentration no more than about 15 weight percent and at a temperature no more than about 100° C. In yet another embodiment the olefinic compound is propylene. Other embodiments will become apparent from the ensuing description.

DESCRIPTION OF THE INVENTION

We have found that incorporation of non-extractable vanadium (i.e., absence of extraneous oxo-vanadium species) into titanosilicalite molecular sieves affords extraordinarily effective catalysts in the epoxidation of oleinc compounds using hydroperoxides as the epoxidizing agent, even where vanadium incorporation is quite low (atom ratio Si/V>100). Hydrogen peroxide can be readily utilized, even at concentrations as low as about 2 weight percent, and epoxidations often take place at a convenient rate at temperatures in the range of 25°–75° C.

The feedstock for this reaction contains olefinic compounds generally. The olefinic compound can be generally described according to the formula

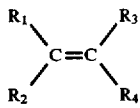

where $R_1$, $R_2$, $R_3$, and $R_4$ may be hydrogen, alkyl, aryl, cycloalkyl, aralkyl, carboxylic acid, carboalkoxy, a halogen, sulfonic acid, sulfonic acid ester, nitrile, sulfone, or ether group. The alkyl, cycloalkyl, arylalkyl, or aryl groups also may contain, e.g., a carboxylic acid grouping, carboxylic ester grouping, halogen, sulfonic acid or sulfonic ester grouping, nitrile, nitro, hydroxyl, ketone, anhydride, amino, hydroxyl, and ether groupings. As can be appreciated, our invention is applicable to an enormous diversity of olefinic compounds. In fact, the major criterion for a suitable feedstock is that is contain a non-aromatic carbon-carbon double bond.

One large group of olefinic compounds which may be used in the practice of our invention are the alkenes, especially those containing between about 2 and 20 carbon atoms. Such alkenes include ethylene, propylene, butene-1, butene-2, isobutylene, the pentenes, heptenes, hexenes, octenes, nonenes, decenes, undecenes, dodecenes, tridecenes, tetradecenes, pentadecenes, hexadecenes, heptadecenes, octadecenes, nonadecenes, and eicosene. Propylene and the 4-carbon olefins are particularly preferred in the practice of this invention. Dimers and trimers—and low-molecular weight oligomers generally—of the lower alkenes such as ethylene, propylene, and the butenes also are suitable olefinic compounds in the practice of this branch of the invention.

The cycloalkenes and the substituted cycloalkenes comprise another class of olefinic compounds which may be used in the practice of our invention. Suitable alkenes include cyclopentene, cyclohexene, cyclooctene, cycloheptene, cyclononene, and cyclodecene. Among other illustrative cyclic olefinic compounds are cyclooctadiene, dicyclopentadiene, methylenecyclopropane, methylenecyclopentane, vinylcyclohexene, methylcyclopentene, ethylcyclopentene, propylcyclopentene, methylcyclohexene, methylcycloheptene, and so forth.

Aryl substituted alkenes also may be used generally and include materials such as styrene, 1-phenyl-1-propene, 1-phenyl-2-propene, 2-phenyl-1-propene, the phenyl butenes, phenyl pentenes, phenyl hexenes, phenyl heptenes, divinylbenzene, indene, stilbene, and so forth.

The olefinic compounds which may be used in the practice of our invention may bear other functional groups, either at the olefinic carbons or, more generally, at a position other than the olefinic carbon. For example, alcohols and ethers thereof may be among the functionalized olefinic compounds used as a feedstock in our invention, including such materials as allyl alcohol, allyl methyl ether, allyl ethyl ether, 2-buten-1-ol, 3-buten-2-ol, 3-buten-1-ol, cinnamyl alcohol, alkyl and aryl ethers of the buten-1-ols, 2-methyl-2-propene-1-ol, alkyl ethers of the latter such as the methyl, ethyl, propyl, and butyl ethers, as well as such ethers as the benzyl and phenyl ethers thereof, all of which serve to illustrate the presence of an hydroxyl or ether group in the olefinic compound. Allyl alcohol and their ethers are particularly important inasmuch as the product, glycidol and glycidyl ethers, are important chemical intermediates.

Haloalkenes also may be used in the practice of this invention, particularly where the halogen is not on an olefinic carbon. For example, allyl chloride and allyl bromide afford as the epoxidation product epichlorohydrin and epibromohydrin, resp., both of which are important articles of commerce.

Olefinic carboxylic acids and their esters are another class of compounds which may be used in the practice of our invention and may be exemplified by such materials as acrylic acid, alpha-methacrylic acid, 2-butenoic acid, 3-butenoic acid, 2-pentenoic acid, 3-pentenoic acid, 4-pentenoic acid, 2-methyl-2-butenoic acid, 3-methyl-2-butenoic acid, 2-methyl-3-butenoic acid, and so forth. Other unsaturated acids of particular mention as olefinic compounds subject to epoxidation by the process of our invention include cinnamic acid, maleic acid, and fumaric acid, and the large class of unsaturated fatty acids and their esters, especially triglycerides, represented by acids such as linoleic acid, linolenic acid, oleic acid, ricinoleic acid, erucic acid, palmitoleic acid, and the like.

Other functional groups may be present in the olefinic compound, especially at the non-olefinic carbons, including such functional groups as the sulfonic acid grouping and their corresponding esters, the nitrile grouping, nitro and ether grouping. Dienes also may be used in epoxidation, especially butadiene. Except in unusual circumstances it must be recognized that dienes can be expected to undergo epoxidation at either C=C bond, hence the selectivity of the epoxidation of dienes can be expected to be low with respect to formation of an epoxide at but one point in the molecule. Consequently dienes, and polyenes more generally, are not favored among the olefinic compounds for this reaction, principally because of the complexity of the resulting reaction mixture. On the other hand, where selectivity of double bond epoxidation is unimportant polyenes may be readily numbered as among the suitable substrates in our invention.

The epoxidizing agent of our invention may be any hydroperoxide, although hydrogen peroxide is preferred by far. Among the organic hydroperoxides may be mentioned the alkyl hydroperoxides, especially tertiary butyl hydroperoxide and, to a lesser extent, the hydroperoxide of ethylbenzene. Peracids form another class of organic compounds furnishing the peroxide linkage and among these peracetic acid, trifluoroperacetic acid, and perbenzoic acid are the most commonly employed peracids.

The primary oxidizing agent which is used in the practice of this invention is hydrogen peroxide, especially as aqueous solutions. Thirty weight percent solutions of hydrogen peroxide in water have been standard in the prior art, but their disadvantage is that of cost. One important advantage of the process of our invention is that our catalysts are effective in bringing about epoxidation even with a feed containing dilute aqueous hydrogen peroxide as the oxidizing agent. Thus, feedstocks containing even 2 weight percent aqueous hydrogen peroxide solutions may be employed to convert the olefinic compounds present to their epoxide in yields in excess of 90% and with virtually 100% efficiency in utilization of hydrogen peroxide. In general, feedstocks containing as little as about 2% and as much as about 70 weight percent hydrogen peroxide may be used, although hydrogen peroxide concentrations of 2–15 weight percent are far more common, and concentrations of 2–10 weight percent are preferred. Where the olefinic compound is epoxidized under heterogeneous conditions, it behooves one to use as concentrated a hydrogen peroxide as is readily available, which generally translates to the use of a 30% hydrogen peroxide solution. Nonetheless, we need to emphasize again that the concentration of the hydrogen peroxide in the feedstock is not a controlling factor in the practice of our invention, that dilute hydrogen peroxide solutions can be readily employed, and that the concentration of hydrogen peroxide used is dictated by secondary factors extraneous to our invention itself We have found titanovanadosilicalites to be particularly effective catalysts in the epoxidation of olefins. What is especially surprising is that even though the vanadosilicalites we tested are quite inactive, and even though in our materials the level of incorporation of vanadium into titanosilicalites is low, the activity of the resulting titanovanadosilicalites significantly surpasses that of the corresponding titanosilicates. Our catalysts of the claimed invention have the empirical formula $(xSiyTizV)O_2$, where $0.96 < x < 0.995$, $0.005 < y < 0.0267$, and $0.0004 < z < 0.01$, and $x+y+z=1$. Expressed in terms of atom ratios of the various combinations, the foregoing is tantamount to $200 < Si/Ti < 36$, and $100 < Si/V < 2500$. It is clear that the amount of vanadium incorporated into our materials is quite small. It is also critical that the vanadium, like the titanium, be incorporated into the resulting molecular sieve, and to ensure the absence of extraneous oxo-vanadium species the catalysts of our invention are exhaustively washed with, e.g., tetrapropylammonium hydroxide to a constant vanadium level. It is believed that in our catalysts that silicon and titanium are present as framework tetrahedral oxide units, and that vanadium either occupies crystal defect sites in the molecular sieve or is situated in a pore balancing framework charge. It also is worth noting that the as-synthesized material, i.e., the titanovanadosilicalite prior to removal of extraneous oxo-vanadium species by exhaustive washing, also is catalytically active in oxidations but without the high selectivity exhibited by our materials. Thus, the extractable vanadium—whatever its exact nature—is an active, unselective oxidation catalyst.

Synthesis of the foregoing materials is readily achieved by hydrothermal crystallization of a gel containing a silicon source, a titanium source, and a vanadium source. Silicon, titanium, and vanadium sources are well known and need not be discussed here. Generally all, or nearly all, of the titanium from the source is incorporated into the resulting molecular sieve. In contrast, it has been observed that only a small fraction of the vanadium from the source is incorporated into the molecular sieve. The molecular sieve can be prepared in either an aqueous medium or an aqueous alcoholic medium, but the latter is strongly favored because of the resulting smaller and more uniform particle size.

As has been previously observed for the titanosilicates, we have found that catalysts of average particle size (i.e., average particle diameter) no more than about 0.5 microns are greatly preferred, and that catalysts with an average particle size of no more than about 0.3 microns are still more highly preferred. When synthesis is performed in an aqueous alcoholic medium the requisite small particle size sieve results upon hydrothermal crystallization without added or special procedures, which is one reason that this synthetic mode is favored.

Catalysts prepared as described above may be used directly or may be ion exchanged with a cation such as an alkali metal or alkaline earth cation. Cation exchange may affect selectivity and sometimes may counter detrimental effects of impurities but this variant is considered optional rather than essential and mandatory. Where cation exchanged material is used exchange with an alkali metal cation, especially that of sodium and potassium, is preferred. Exchange with an alkaline earth metal cation is another variant, one in which the use of magnesium and calcium is preferred. The metal exchanged commonly is at a level between about 0.05 and about 0.25 weight percent based on the titanovanadosilicalite.

Olefinic compounds are oxidized using principally hydrogen peroxide as the oxidizing agent in the presence of the aforedescribed catalyst under epoxidation reaction conditions. Such reaction conditions include a temperature as low as about 0° C. up to as high as about 100° C. Epoxidation may be conducted at atmospheric pressure; a major reason to perform the epoxidation at elevated pressure is to increase the solubility of gaseous reactants in the reaction medium. For example, where propylene is epoxidized without the use of a cosolvent increased pressure leads to an increased solubility of the propylene in aqueous solution with an increase in overall rate of propylene epoxide formation. In a greatly prepared variant epoxidation is performed in aqueous alcohols, especially alcohols having fewer than 5 carbons. We particularly prefer conducting epoxidations in aqueous methanol as the solvent system. In another variant the feed contains from 2 up to 200 ppm potassium cation, preferably between about 5 and 20 ppm.

Epoxidation may be performed according to our invention in either a batch or continuous mode. For example, in a batch mode the olefinic compound, either alone or in an organic solvent, is mixed with an aqueous hydrogen peroxide solution in the presence of an effective amount of our catalyst. The amount of titanovanadosilicalite used per mole of carbon-carbon double bond to be epoxidized may be as low as about 3 grams per mole. There is no theoretical limit to the maximum amount of titanovanadosilicalite to be used, although as a practical matter there is no benefit from using more than about 30 grams per mole of carbon-carbon double bond. The reaction mixture is stirred well at temperatures between 0° C. up to as high as about 100° C. The hydrogen peroxide may be present at a concentration as low as about 2 weight percent and as high as about 50 weight percent. Whether the hydrogen peroxide or the olefinic compound is present in excess depends upon the nature of the olefinic compound as well as its cost. For example, where propylene is being epoxidized, unreacted gaseous propylene may be readily recovered and recycled. In such an instance it is advantageous to have the olefinic compound in molar excess, perhaps as much as 2–10 moles per mole of hydrogen peroxide. However, where a rather expensive, or relatively unavailable olefinic compound is being epoxidized, it may be highly advantageous to use hydrogen peroxide in molar excess, perhaps in amounts as little as 5–10% molar excess, although molar ratios of up to 10 may be employed. In general, then, the molar ratio of olefinic compound to hydrogen peroxide may range from 1:10 to 10:1.

Where the reaction is performed in a continuous mode one may employ any of the conventional process techniques currently known. These include use of a fixed bed process, a continuous stirrer tank reactor process, a radial bed reactor process, and so on. In such cases the catalyst of our invention may be used as pellets, extrudates, spheres, and the like. When our catalyst is used in such forms it is preferable to incorporate a binder for preserving and enhancing catalyst integrity. Conventional binders include silica, alumina, silica-alumina, and various clays, but since such conventional materials are well known to those skilled in the binder art no further detailed discussion will be given.

The following examples merely illustrate the process of our invention and are not intended to limit it in any way. Variants of the following examples may be readily envisioned by the skilled worker and are deemed to be within the scope of our invention.

EXAMPLES

Preparation of a Titanovanadosilicalite in Aqueous Medium

The catalyst preparation is adapted from a vanadium-silicalite procedure found in the literature (Rigutto M. S., van Bekkum H, Appl. Catal. 1991. 68, L1). In our preparation, 175 g colloidal silica (Ludox AS-40) was treated with 44.73 g $NH_4OH$. Separately, a solution was prepared containing 5.08 g $VOSO_4 \cdot 3H_2O$ and 9.00 g $TiCl_3$ (20% Ti) in 102.69 g distilled water. This solution was added dropwise to the silica sol while stirring the reaction mixture with a high speed mixer. A brown-yellow gel of pourable consistency resulted, having a pH of 10.5. After stirring for one-half hour, 97.65 g tetrapropylammonium hydroxide (TPAOH) (40%) was added, which changed the nature of the reaction mixture from gel-like to solution-like, and brought the pH up to 12.80. The solution was stirred for another 45 minutes at which time the pH was 12.54. The mixture was placed in a 600 ml Parr stirred reactor, ramped up to 170° C. over a 2 hour period, and then digested at 170° C. for 96 hours. The off-white product was filtered from a yellow mother liquor and washed thoroughly. An orange colored contaminant was also observed and was believed to be a hydrated form of $V_2O_5$. The material was extracted with a TPAOH solution (pH=11.5) to remove the extraneous oxo-vanadium species. The material was then calcined at 500° C. The material was re-extracted with TPAOH solution and calcined at 500° C. Analyses were performed on this material.

Gel Molar Ratios: 100 $SiO_2$: 2 $VOSO_4 \cdot 3H_2O$: 1 $TiCl_3$: 66 $NH_4OH$ :16.5 TPAOH:1359 $H_2O$

Product Analysis:

XRD showed the product to have the silicalite structure

| | |
|---|---|
| Si/V = 867 | Particle size: 3–10μ |
| Si/Ti = 103 | Surface Area: 319 m²/g |
| Si/Al = 1091 | Pore Volume: 0.19 g/cc |
| | Pore Diameter: 24 Å (Average) |

Because of the extraction procedure used, one can confidently conclude that extraneous oxovanadium species have been removed and that the titanium and vanadium remaining in the material are intimately associated with the framework as incorporated framework species, as strongly bound species (e.g., occupation of framework defect sites), or as framework charge-balancing species.

Preparation of a Titanovanadosilicalite in an Aqueous Alcoholic Medium

The literature (Zeolites, vol. 14, p558) suggests that the presence of alcohol in a silicalite synthesis mixture will result in smaller particles. We adapted this method for the synthesis of titanium-vanadium silicalite materials.

A mixture of tetraethyl orthosilicate (TEOS), 455 g, and 100 g isopropyl alcohol (IPA) was cooled to <5 C. To this a mixture of 100 g of 40 wt. % (TPAOH) and 100 g water was added dropwise in order to partially hydrolyze the silicon source. To this a mixture of 22.4 gm titanium butoxide in 22.4 g IPA was added dropwise with vigorous stirring. After the addition the titanium source was completed, 1.428 g of VOSO4×3H2O in 7 g water was added to the synthesis mixture. The liquid was stirred for about 1 hour at room temperature, after which 300 g of 40 wt. % TPAOH in 1100 g distilled water was added to complete the hydrolysis at 80 C. for about 6 hours.

Gel Molar Ratios: 100 Si 3Ti 0.3V 36TPA 152 IPA 3680 H2O

The gel was added to two different autoclaves. One crystallization was in a stirred PARR autoclave, another one under static conditions in a Teflon-lined autoclave. The crystallization was permitted to proceed under hydrothermal conditions (175 C., 4–6 days, 250–300 psig autogenous pressure). A crystalline solid was obtained from each autoclave and was centrifuged at 5000 rpm washed with distilled water, dried, and calcined at 550 C. After calcination, the samples were extracted at pH=11 with TPAOH. After washing, drying, and calcination the samples were characterized and tested.

Product Analysis (stirred conditions): XRD characterization showed that the product had the silicalite structure. IR shows strong 960 cm–1 band.

Si/Ti=36
Si/V=999
Particle size: Uniform 0.2 micron
SA: 384 sq m/g
Total Pore Volume: 0.2876 cc/g
Average pore radius 14.95 Angstrom
Langmuir Surface: 600 sq m/g
Ti-V-Silicalite-1 Product analysis (static Conditions)

XRD characterization showed that the product had the silicalite structure. IR shows strong 960 cm–1 band.
Si/Ti=42.67
Si/V=2031
Particle size: Uniform<0.2 micron
SA: 360 sq m/g
Total Pore Volume: 0.2755 cc/g
Average pore radius 14.5 Angstrom

Preparation of V-Silicalite

V-Silicalite was prepared by employing the van Bekkum gel composition: 100 $SiO_2$:11 $NH_3$: 11 TPAOH:2 $VOSO_4 \cdot 3H_2O$: 1200 $H_2O$. 301.9 g Ludox AS-40 was placed in a 1-liter beaker. The colloidal silica was stirred as 12.78 g $NH_4OH$ solution (29.2% NH3) was added. Then 9.78 g $VOSO_4 \cdot 3 H_2O$ was dissolved in 176.0 g distilled water. This solution was added dropwise to the Ludox/ ammonium hydroxide mixture. The 111.60 g TPAOH (40% solution) was added to the reaction mixture, resulting in a brown solution. The mixture was stirred for 30 minutes with a high-speed mixer. The resulting brown solution-like mixture was placed in a 600 ml Parr stirred-reactor. The gel was digested at 180° C. for 69 hours.

The reaction products were a yellow-green mother liquor, which was filtered away from a light bluish-white solid. The solid was washed thoroughly with distilled water. Before use in catalytic tests, the material was calcined at 475° C. for 20 hours, as recommended in the van Bekkum procedure.

Product Analysis

XRD showed the product to have the silicalite structure

Si/V=226
Si/Al 1130
Particle Size=3–10μ

V-Silicalite Preparation (Small Particle Size) in Aqueous-Alcoholic Medium

A mixture of tetraethyl orthosilicate (TEOS), 455 g. and 100 g isopropyl alcohol (IPA) was cooled to <5 C. To this a mixture of 100 g of 40 wt. % (TPAOH) and 100 g water was added dropwise in order to partially hydrolyze the silicon source. To this a mixture 14 g of $VOSO_4 \times 3H_2O$ in 55 g water was added dropwise with vigorous stirring. The liquid was stirred for about 1 hour at room temperature, after which 300 g of 40 wt. % TPAOH in 1100 g distilled water was added to complete the hydrolysis at 80 C. for about 6 hours.

Gel Molar Ratios: 100 Si 3V 36TPA 152 IPA 3680 H2O

The gel was added under static conditions in a Teflon-lined autoclave. The crystallization was permitted to proceed under hydrothermal conditions (150 C., 4 days, 250–300 psig autogenous pressure). A crystalline solid was obtained autoclave and was centrifuged at 5000 rpm, washed with distilled water, dried, and calcined at 550 C. The Si/V ratio was 265. After calcination, the samples were extracted at pH=11 with TPAOH. After washing, drying, and calcination the samples were characterized and tested.

Product Analysis:

XRD characterization showed that the product had the silicalite structure.

Si/V=950
Particle size:<0.2 micron (average 147)

Ti-Silicalite Preparation (Small Particle Size) in Aqueous-Alcoholic Medium

A mixture of tetraethyl orthosilicate (TEOS), 455 g. and 100 g. isopropyl alcohol (IPA) was cooled to <5 C. To this a mixture of 100 g of 40 wt. % (TPAOH) and 100 g water was added dropwise in order to partially hydrolyze the silicon source. To this a mixture 22.4 g Titanium (IVO butoxide in 100 g isopropyl alcohol was added dropwise with vigorous stirring. The liquid was stirred for about 1 hour at room temperature, after which 300 g of 40 wt. % TPAOH in 1100 g distilled water was added to complete the hydrolysis at 80° C. for about 6 hours.

Gel Molar Ratios: 100 Si 3Ti 36TPA 152 IPA 3680 H2O

The gel was added under static conditions in a Teflon-lined autoclave. The crystallization was permitted to proceed under hydrothermal conditions (150 C., 4 days, 250–300 psig autogenous pressure). A crystalline solid was obtained autoclave and was centrifuged at 5000 rpm, washed with distilled water, dried, and calcined at 550 C. The calcinated samples were characterized. Potassium ion exchanged and tested.

Product Analysis:

XRD characterization showed that the product had the silicalite structure.

Si/Ti=553
Particle size: 0.2 micron

Potassium Ion Exchange(general method)

10 gms of the metal(Ti,V) Silicalite sample was exchanged with 100 cc of a 1 molar aqueous solution of Potassium Chloride at 80 C. 6 hrs. After centrifuged the crystals washed 3 times 100 cc 60 Centigrade water. After separation of silicalite from water dry at 100 C. vacuum overnight. The potassium level of Ti-V-Silicalite after Potassium ion exchange is 0.11 wt % Potassium.

Catalytic Testing

Hydrogen peroxide (40 g, 30 weight percent concentration of $H_2O_2$), 200 g methanol, and 5 g catalyst were loaded to 300 cc stainless steel autoclave. At room temperature was charged 80 g liquid propylene with nitrogen. The pressure was increased with nitrogen to 500 psi and the temperature was increased to 40° C. over 30 min. The molar ratio of propylene to $H_2O_2$ under these conditions is 5; $H_2O_2$ is the limiting reagent. Liquid samples were taken at 1,3, 4 and 6 hrs. After 6 hrs the reaction was shut down and the autoclave was depressured. The remaining liquid was sampled again. This final sample is termed the "shut-down" sample.

The samples were analyzed by GC. The yield of propylene oxide is expressed as concentration of propylene oxide in the sample to the maximum theoretical concentration of propylene oxide. (Yield=[Propylene oxide]/[Propylene$_{oxide}$] $_{max\ theoretical}$) The selectivity to propylene oxide is calculated as the ratio of the concentration of propylene oxide in the sample to the sum of the concentrations of propylene oxide, metboxy-propylene glycols, and propylene glycol. The batch autoclave results for the Ti-V silicalites prepared via aqueous and non-aqueous routes are shown below.

TABLE 1

Oxidation of Propylene Catalyzed by Framework-Substituted Silicalites

| Molecular Sieve | Ti—V-Silicalite | | | | V-Silicalite | | | Ti-Silicalite | | |
|---|---|---|---|---|---|---|---|---|---|---|
| Average Particle Size (nm) | >3000 | 130 | | 130 | >3000 | 150* | | 166* | | 200 |
| K exchange[b] | No | Yes | Yes | Yes | Yes | Yes | | Yes | Yes | Yes |
| Temp °C. | 60 | 60 | 40 | 35 | 35 | 40 | | 40 | 40 | 35 | 35 |
| Time (hrs) | 6 | 6 | 6 | 6 | 6 | 6 | | 6 | 6 | 6 | 6 |
| Si/Ti | 103 | 103 | 36 | 36 | 44 | 0 | | 0 | 54 | 54 | 55.35 |
| Si/V | 867 | 867 | 999 | 999 | 2026 | | 311 | 265** | 0 | 0 | 0 |
| Propylene oxide yield, % | 62 | 80 | 91 | 94 | 95 | 16 | | 0 | 64 | 71 | 48 |
| Propylene conversion, % | 84 | 99 | >99 | 98 | >99 | 17 | | 0 | 87 | 74 | 62 |

TABLE 1-continued

Oxidation of Propylene Catalyzed by Framework-Substituted Silicalites

| Molecular Sieve | Ti—V-Silicalite | | | | | V-Silicalite | | Ti-Silicalite | | |
|---|---|---|---|---|---|---|---|---|---|---|
| Selectivity | 73 | 80 | 87 | 95.9 | 96.8 | 94 | 0 | 71 | 95.3 | 78 |
| $H_2O_2$ conversion, % | 95.3 | 98 | 99 | 99.4 | 98.8 | 29 | | 98.4 | 78.8 | |

Test Conditions:
5 gms catalyst 40 g 30 wt % Hydrogen peroxide 200 g methanol and add 80 gms liquid propylene 450 cc Parr Reactor with mechanical stirrer (500 rpm)
\* = used 1 gm catalyst
\*\* = Si/V ratio 265; after TPAOH extraction room temperature 8 hrs pH = 10.5 Si/V = 950.
aPurchased from National Chemical Laboratory, Puna-411, India as reference TS-1. Particle size was not uniform; results varied batch-to-batch.
bK exchanged material had 0.11–0.14 weight percent potassium

What is claimed is:

1. A process for the epoxidation of a carbon-carbon double bond in an olefinic compound comprising reacting under epoxide-forming conditions the olefinic compound in a feedstock with a hydroperoxide in the presence of a catalyst of a crystalline titanovanadosilicalite molecular sieve composition free of extraneous oxo-vanadium species, where the titanium and silicon are present as framework tetrahedral oxide units, said sieve having a unit empirical formula on an anhydrous basis of $(xSiyTizV)O_2$, where x has a value between about 0.96 and about 0.995, y has a value between about 0.005 and about 0.0267, and z has a value between about 0.0004 and about 0.01 and $(x+y+z)=1$.

2. The process of claim 1 where epoxide-forming conditions include a temperature between about 0° C. and about 100° C.

3. The process of claim 1 where the hydroperoxide is hydrogen peroxide.

4. The process of claim 3 where the hydrogen peroxide is at a concentration from about 2 weight percent up to about 50 weight percent.

5. The process of claim 3 where the hydrogen peroxide is at a concentration between about 2 and about 15 weight percent.

6. The process of claim 5 where the hydrogen peroxide is at a concentration between about 2 and about 10 weight percent.

7. The process of claim 1 where the olefinic compound is an alkene or cycloalkene.

8. The process of claim 7 where the alkene is propylene.

9. The process of claim 7 where the cycloalkene is cyclohexene.

10. The process of claim 1 where the olefinic compound is an alcohol.

11. The process of claim 10 where the alcohol is allyl alcohol.

12. The process of claim 1 where the olefinic compound is a carboxylic acid, a carboxylic acid anhydride, or an ester of a carboxylic acid.

13. The process of claim 12 where the carboxylic acid or an ester thereof is maleic acid, fumaric acid, esters thereof, or any mixture thereof.

14. The process of claim 1 further characterized in that the olefinic compound is reacted as a solution in an organic solvent.

15. The process of claim 1 where the catalyst has an average particle size no more than about 0.5 microns.

16. The process of claim 15 where the catalyst has an average particle size no more than about 0.3 microns.

17. The process of claim 1 where the feedstock contains from about 2 up to about 200 parts per million potassium cations.

\* \* \* \* \*